United States Patent
Carton et al.

(10) Patent No.: US 8,867,700 B2
(45) Date of Patent: Oct. 21, 2014

(54) METHOD FOR ESTIMATING AND CORRECTING SCATTERING IN MAMMOGRAPHY

(75) Inventors: Ann-Katherine Carton, Issy-les-Moulineaux (FR); Serge Louis Wilfrid Muller, Guyancourt (FR); Remy Andre Klausz, Neuilly sur Seine (FR); Giovanni John Jacques Palma, Issy-les-Moulineaux (FR); Razvan Gabriel Iordache, Paris (FR); Sylvie Puong, Paris (FR)

(73) Assignee: General Electric Company, Schenectady, NY (US)

( * ) Notice: Subject to any disclaimer, the term of this patent is extended or adjusted under 35 U.S.C. 154(b) by 328 days.

(21) Appl. No.: 13/281,828

(22) Filed: Oct. 26, 2011

(65) Prior Publication Data

US 2012/0106697 A1     May 3, 2012

(30) Foreign Application Priority Data

Oct. 29, 2010   (FR) ...................................... 10 58961

(51) Int. Cl.
| | |
|---|---|
| *H05G 1/64* | (2006.01) |
| *G06K 9/60* | (2006.01) |
| *A61B 6/00* | (2006.01) |
| *G21K 1/10* | (2006.01) |
| *A61B 6/06* | (2006.01) |
| *G03B 42/02* | (2006.01) |

(52) U.S. Cl.
CPC ................ *A61B 6/4035* (2013.01); *A61B 6/502* (2013.01); *A61B 6/542* (2013.01); *A61B 6/4291* (2013.01); *A61B 6/488* (2013.01); *G21K 1/10* (2013.01); *A61B 6/06* (2013.01); *G03B 42/02* (2013.01); *A61B 6/5282* (2013.01)
USPC ............................ 378/37; 378/98.12; 382/130

(58) Field of Classification Search
CPC ........... G21K 1/00; G21K 1/02; G21K 1/025; G21K 1/10; G01N 15/0211; A61B 6/06; G06T 11/005; H01J 2237/31791
USPC .......... 378/37, 51, 56, 52, 68, 67, 91, 95, 98, 378/98.12, 145, 154, 155, 204, 205, 207, 378/210; 382/128, 130, 131
See application file for complete search history.

(56) References Cited

U.S. PATENT DOCUMENTS

| | | | |
|---|---|---|---|
| 4,286,156 | A | 8/1981 | Wagner |
| 4,549,307 | A | 10/1985 | Macovski |

(Continued)

OTHER PUBLICATIONS

French Search Report issued on Mar. 31, 2011 in connection with FR Patent Application 1058961 filed on Oct. 29, 2010.
Rezentes, P.S. "Mammography grid performance", Radiology 210, 227-232 (1999).
Wagner, F.C., Macovski, AK and Nishimura D.G. "Dual-energy x-ray projection imaging: two sampling schemes for the correction of scattered radiation", Med. Phys. vol. 15, p. 732-748 (1988).

(Continued)

*Primary Examiner* — Anastasia Midkiff
(74) *Attorney, Agent, or Firm* — Global Patent Operation; Marc A. Vivenzio

(57) ABSTRACT

A method for correcting at least one image of an object obtained with a mammography system is provided. The method comprises: acquiring a pre-exposure image of an object to determine the acquisition conditions for main images, the pre-exposure image comprising regions corresponding to the projection of radio-opaque elements, wherein a mask comprising radio-opaque elements is in an acquisition position; acquiring the main images resulting from the passing through the object of X-rays at higher doses than the dose used for acquisition of the pre-exposure image, wherein the mask comprising radio-opaque elements is in a retracted position; extracting regions from the pre-exposure image which correspond to the projection of radio-opaque elements; and determining the contribution of X-ray scatter at every point of the at least one image of the object, on the basis of the regions extracted from the pre-exposure image.

9 Claims, 2 Drawing Sheets

(56) References Cited

U.S. PATENT DOCUMENTS

| | | | |
|---|---|---|---|
| 4,656,650 A | | 4/1987 | Kikuchi et al. |
| 4,677,681 A | | 6/1987 | Klausz |
| 4,741,009 A | | 4/1988 | Yamagata et al. |
| 4,823,370 A | | 4/1989 | Kikuchi |
| 4,837,796 A | * | 6/1989 | Ema ............................ 378/154 |
| 4,878,186 A | | 10/1989 | Gagnon |
| 4,916,722 A | | 4/1990 | Ema |
| 4,918,713 A | | 4/1990 | Honda |
| 5,050,198 A | | 9/1991 | Honda |
| 5,615,279 A | | 3/1997 | Yoshioka et al. |
| 5,684,851 A | | 11/1997 | Kurbatov et al. |
| 6,292,536 B1 | | 9/2001 | Chichereau et al. |
| 6,748,047 B2 | | 6/2004 | Gonzalez Trotter et al. |
| 7,372,936 B2 | | 5/2008 | Nukui |
| 2005/0286681 A1 | * | 12/2005 | Bernhardt et al. ............... 378/62 |
| 2007/0019847 A1 | * | 1/2007 | Inoue et al. .................... 382/128 |
| 2009/0304142 A1 | | 12/2009 | Ruimi et al. |
| 2010/0140485 A1 | * | 6/2010 | Mishra et al. .............. 250/363.1 |

OTHER PUBLICATIONS

Shaw et al., "A technique of scatter and glare correction for videosensitometric studies in digital subtraction videoangiography," Radiology 142, pp. 209-213, Jan. 1982.

Fahrig et al., "Performance of glass fiber antiscatter devices at mammographic energies," Medical Physics, Volume No. 21, Issue No. 8, pp. 1277-1282, Aug. 1994.

Boone et al., "Grid and slot scan scatter reduction in mammography: Comparison by using Monte Carlo techniques," Radiology, Volume No. 222, Issue No. 2, pp. 519-527, Feb. 2002.

Aslund et al., "Scatter rejection in multislit digital mammography," Medical Physics, Volume No. 33, Issue No. 4, pp. 933-940, Apr. 2006.

Zhu et al., "Scatter correction for cone-beam CT in radiation therapy", Medical Physics, Volume No. 36, Issue No. 6, pp. 2258-2268, Jun. 2009.

Shaw, et al., "Quantitative Digital Subtraction Angiography: Two Scanning Techniques for Correction of Scattered Radiation and Veiling Glare", Radiology 1985; vol. 157, No. 1, pp. 247-253.

* cited by examiner

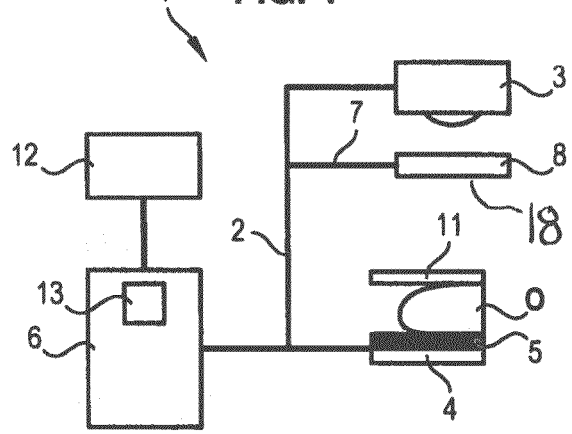
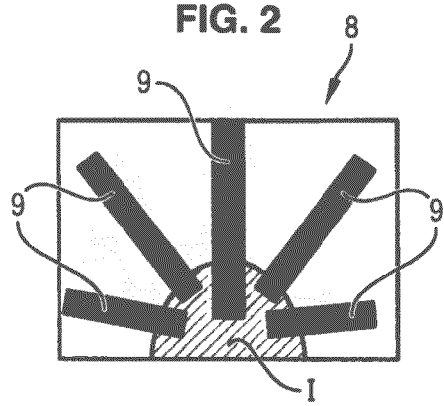
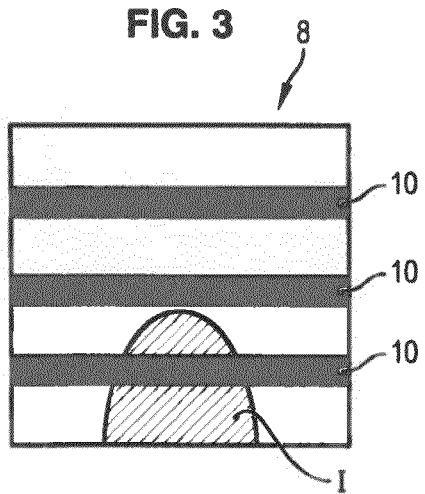
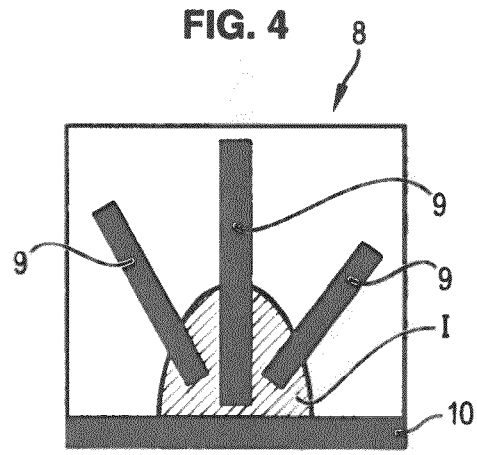

METHOD FOR ESTIMATING AND CORRECTING SCATTERING IN MAMMOGRAPHY

BACKGROUND OF THE INVENTION

1. Field of the Invention

Embodiments of the present invention relate to X-ray medical imaging, and in particular breast radiography or mammography. Embodiments of the present invention notably relate to X-ray mammography devices comprising image processing units.

2. Description of the Prior Art

Conventional X-ray imaging systems allow the acquiring of projection images of an object of a subject, typically a female patient's breast, via the passing of X-rays through the object.

However, when X-rays pass through the object, a phenomenon of scattering is observed, resulting from interaction between the X-rays and the different constituent materials of the object.

This scattering of X-rays has an impact on the image obtained which then exhibits degradations.

Several approaches have been put forward to reduce or compensate this scattering of X-rays, either using physical elements or using pre or post-acquisition processing methods.

The approaches using physical elements make use of anti-scatter mechanical grids arranged between the object and the X-ray sensor, the mechanical grids being formed to absorb all or part of scattered X-ray radiation. The document "Mammography grid performance", Radiology 210, 227-232 (1999) by P. S. Rezentes, A. de Almeida and G. T. Barnes presents an example of anti-scatter mechanical grids. However, these mechanical grids absorb part of the emitted X-rays, and it is therefore necessary to increase the emitted X-ray dose to maintain a good quality image. In addition, these anti-scatter grids do not fully prevent scattered radiation; the transmission of scattered radiation through said anti-scatter grids under standard mammography conditions being of the order of 15 to 20%.

A method for estimating and correcting this residual scattered radiation has already been proposed and is described in document U.S. Pat. No. 4,677,681. This method is based on the use of masks opaque to X-ray radiation inserted in the beam between the source and the examined object, so as to estimate the quantity of X-ray radiation scattered by the object.

This method nonetheless requires the acquisition of at least one additional image compared with conventional imaging, this image being solely intended to determine the contribution of scattered radiation to the image insofar as the images taken in the presence of opaque elements cannot be used for diagnosis. This aspect could be acceptable for the acquisition of sequences of several images, but this is not so for ordinary radiography e.g. mammography in which it is sought to record a single image.

BRIEF SUMMARY OF THE INVENTION

Embodiments of the present invention propose a solution which does not have these shortcomings.

According to an embodiment of the present invention, a method for correcting at least one image of an object obtained with a mammography system comprising an X-ray emitting source arranged facing a detector, the object being positioned between the source and the detector, the acquisition conditions of the images being determined by using the characteristics of a pre-exposure image of the object, is provided. The method comprises: acquiring a pre-exposure image of an object to determine the acquisition conditions for main images, the pre-exposure image comprising regions corresponding to the projection of radio-opaque elements, wherein a mask comprising radio-opaque elements is in an acquisition position, the acquisition position being when the mask is in the X-ray pathway leading from the source to the object; acquiring the main images resulting from the passing through the object of X-rays at higher doses than the dose used for acquisition of the pre-exposure image, wherein the mask comprising radio-opaque elements is in a retracted position, the retracted position being when the mask is outside of the X-ray pathway leading from the source to the object; extracting regions from the pre-exposure image which correspond to the projection of radio-opaque elements; and determining the contribution of X-ray scatter at every point of the at least one image of the object, on the basis of the regions extracted from the pre-exposure image.

According to another embodiment of the present invention, a method for the mammography of an object using a system comprising an X-ray emitting source arranged facing a detector, the object being positioned between the source and the detector, the acquisition conditions of at least one image of the object being determined using the characteristics of a pre-exposure image of the object, is provided. The method comprises: acquiring a pre-exposure image of the object, the pre-exposure image resulting from the passing through the object of a first dose of emitted X-rays, and comprising regions corresponding to the projection of radio-opaque elements, wherein a mask comprising radio-opaque elements is in an acquisition position, the acquisition position being when the mask is in the X-ray pathway leading from the source to the object; acquiring main images resulting from the passing through the object of an at least one dose of emitted X-rays, the at least one dose being greater than the first dose, wherein the mask comprising radio-opaque elements is in a retracted position, the retracted position being when the mask is outside of the X-ray pathway leading from the source to the object; extracting regions from the pre-exposure image which correspond to the projection of radio-opaque elements: determining X-ray scatter in the object from the regions extracted from the pre-exposure image; defining coefficient(s) resulting from the difference in dose between the first dose of emitted X-rays and the at least one dose of emitted X-rays that are great than the first dose; using the coefficient(s) to scale the contribution of X-ray scatter to the image of the object; and subtracting the term of scattered X-ray radiation from the main images to obtain a final scatter-free image.

According to another embodiment of the present invention, a system for the mammography of an object using X-rays is provided. The system comprises: an X-ray emission source; a detector arranged facing the source, wherein the object is positioned between the source and the detector; a mask comprising radio-opaque elements; and a processing unit comprising a computer configured to extract regions from a pre-exposure image of the object which correspond to the projection of radio-opaque elements and to determine the contribution of X-ray scatter at every point of at least one image of the object on the basis of the regions extracted from the pre-exposure image, wherein the pre-exposure image of the object is acquired when the mask comprising radio-opaque elements is in an acquisition position, the acquisition position being when the mask is in the X-ray pathway leading from the source to the object, and wherein main images resulting from the passing through the object of X-rays at higher doses than the dose used for acquisition of the pre-exposure image are acquired when the mask comprising radio-opaque elements is in a retracted position, the retracted position being when the mask is outside of the X-ray pathway leading from the source to the object.

BRIEF DESCRIPTION OF THE SEVERAL VIEWS OF THE DRAWINGS

Other characteristics, purposes and advantages of the invention will become apparent from the following description which is solely illustrative and is non-limiting, and is to be read with reference to the appended drawings, in which:

FIG. 1 illustrates an X-ray imaging system according to an embodiment of the present invention;

FIGS. 2, 3 and 4 illustrate grids according to an embodiment of the present invention;

DETAILED DESCRIPTION OF THE INVENTION

Figure 5:
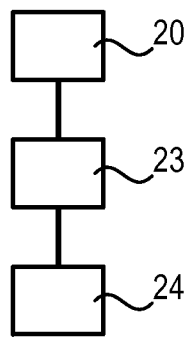
FIGS. 5 and 6 show variants of an image correction method according to an embodiment of the present invention.

FIG. 1 shows a mammography system according to an embodiment of the invention,

Such as illustrated in this figure, the system 1 comprises an arm 2 on which an X-ray emission source 3 and a detector 4 facing the source 3 are respectively attached.

The source 3 is adapted to emit different values of X-ray dose, notably dose values allowing the acquisition of pre-exposure images and of conventional images whose acquisition conditions are determined in relation to the data acquired from the pre-exposure image. These X-rays emitted by the source 3 are captured by the detector 4 which converts the same into signals and generates images from these signals.

A pre-exposure image is an image acquired with a relatively low dose of emitted X-rays compared with the images conventionally used to obtain the final picture, and allowing the acquisition conditions to be determined for subsequent images by determining the attenuation properties in particular of the object that it is desired to be visualized, as described in document U.S. Pat. No. 6,292,536.

The use of low doses makes it possible to avoid excessive increase in the X-ray dose to which the targeted object is exposed.

The system 1 also comprises a support 5 adapted for arranging an object O of a subject thereupon, typically the breast for mammography, the support 5 being arranged so that the object O is positioned between the source 3 and the detector 4.

A compression plate 11 is used to compress the object O on the support 5.

The system 1 such as illustrated further comprises: a processing unit 6 adapted to perform the processing of signals sent by the detector 4, and the correcting of images; and an actuator 7 joined to a mask 8 comprising radio-opaque elements, the actuator 7 typically being a mechanical element used to move the mask 8 between an acquisition position in which it lies between the object O and the source 3, and a retracted position in which it lies outside the X-ray pathway leading from the source 3 to the object O.

This actuator 7 may achieve movement of the mask 8 in automated fashion or it may be driven by the user.

The movement of the mask 8 may take place by rotation about a horizontal or vertical axis, or by translation. The translational movement of the mask 8 may be achieved for example via a rapid return drum 18 on which the mask 8 is wound, and whose rotation causes movement of the mask 8 to place it in position between the object O and the source 3 or to place it in retracted position.

The mask is then formed in a flexible material to allow winding thereof around the drum.

The processing unit typically comprises a computer 13 which may consist of one or more computers for example, one or more processors, micro-controllers, etc.

The computer 13 allows the performing of image processing and correction operations, typically of a pre-exposure image so as to extract regions from the pre-exposure image e.g. regions corresponding to the projection of radio-opaque elements, and to determine the contribution of scattered X-ray radiation to the image of the object O on the basis of these regions extracted from the pre-exposure image.

The processing unit 6 such as illustrated is coupled with a memory unit 12 which can be integrated in or separate from the processing unit 6. This memory unit allows the storing of data such as images, and may be a hard disk for example, CD-ROM, ROM/RAM memory or any other adapted means.

The processing unit 6 may comprise a reader device (not illustrated) e.g. a CD-ROM reader to read the instructions of the imaging method (which is described in the remainder hereof) from an instruction medium (not shown) e.g. a diskette or CD-ROM. As a variant, the processing unit 6 carries out the instructions of the imaging method (described in the remainder hereof) stored in firmware (not illustrated).

The mask 8 consists of radio-opaque elements, typically made in materials with high atomic number (between 20 and 40 or greater than 70) and with a density greater than 5 such as lead, gold, copper or tungsten, and rigidly assembled to maintain relative constant positioning between each element.

These elements may be arranged in several configurations, of which examples are described below. Their shapes may vary: they may be rectilinear, curved, containing parallelepiped or circular sections, or any other suitable shape.

The radio-opaque elements of the mask 8 typically cover no more than 10% of the projection surface of the X-rays emitted by the source 3, so as not to perturb acquisition of the pre-exposure image with respect to its function regarding the determination of acquisition conditions for subsequent images, and so that X-ray scattering remains substantially unchanged with or without the mask 8.

The mask 8 is typically arranged at the output of the X-ray source or in the vicinity of the object concerned, for example at the compression plate 11 for a mammography system.

The mask 8 may be formed for example by cutting openings in a plate in a radio-opaque material using LASER for example or techniques similar to those used to form printed circuits. According to another variant, the radio-opaque elements can be individually fixed to a support in material substantially transparent to X-rays.

Preferably, the actuator 7 adapts the positioning of the mask 8 to the shape of the object O. For example, if the object O is a breast, the mask 8 is typically arranged so that it lies substantially perpendicular to the typical contour of a breast.

FIG. 2 illustrates an embodiment of the mask 8 comprising radial radio-opaque elements 9. The radial radio-opaque elements are typically arranged radially starting from one of the sides of the mask 8 substantially corresponding to a central point of the object O The projection I of the object O onto the mask 8 is therefore illustrated, the organ typically being a breast of a subject.

FIG. 3 shows another variant of the mask 8 which comprises parallel radio-opaque elements elements 10, arranged here in the direction of the length of the mask 8. Other embodiments are evidently possible, notably embodiments in which the radio-opaque elements are arranged parallel in the direction of the width of the mask 8, or tilted at a given angle.

FIG. 4 shows a variant of the mask 8 comprising radial radio-opaque elements together with a parallel radio-opaque element 10 which, here, is arranged along an edge of the mask 8.

In the three illustrated embodiments, it can be seen that the projection I of the object O onto the mask 8 is at least partly covered by the radio-opaque elements 9 or 10, to ensure that the image of the object O comprises regions corresponding to the projection of radio-opaque elements.

It can also be seen that the different opaque elements 9 and 10 are spaced apart to avoid intersections which would produce concentration areas of these opaque elements 9 and 10.

FIG. 5 is a schematic illustration of the steps of one embodiment of a method for correcting images of an object obtained using an X-ray mammography system of the invention.

The method such as illustrated comprises: an acquisition step 20 to acquire a pre-exposure image of the organ, said pre-exposure image comprising regions corresponding to the projection of radio-opaque elements such as described previously; an extraction step 23 to extract regions from the pre-exposure image which correspond to the projection of radio-opaque elements, a determination step 24 to determine X-ray scattering in the object on the basis of the said regions extracted from the pre-exposure image.

The acquisition step 20 comprises obtaining a pre-exposure image of the targeted object O, via, the emission of X-rays through the object O at acquisition step 20.

The obtaining of the pre-exposure image is performed via the emission of X-rays from the X-ray emission source 3 which pass through the object O and are then captured by the detector 4 which captures those X-rays which passed through the object O and coverts the same into signals. A relatively low dose of X-rays is emitted, this pre-exposure image being taken to determine the acquisition conditions for subsequent images that are used for diagnosis.

The extraction step 23 comprises identifying and extracting regions from the previously acquired pre-exposure image that correspond to projections of the radio-opaque elements of the mask 8.

The determination step 24 comprises using the projections of radio-opaque elements to determine the scattering of X-rays on passing through the object O.

If there is no scattering, the dose in the regions which correspond to the projection of radio-opaque elements of the mask 8 should be zero, the X-rays being blocked by the radio-opaque elements.

However, doses are observed in these regions which correspond to the scattering of X-rays by regions adjacent to the regions corresponding to the projection of radio-opaque elements.

Therefore, by identifying these doses and processing the corresponding signals using a processing unit 6 or computer 13, it is possible to perform an interpolation of X-ray scatter over the entire object O.

The determination of the scattering of X-rays when they pass through the object O can be made using linear, bilinear or spline interpolation methods, these methods being well known to the person skilled in the art.

The document "Dual-energy x-ray projection imaging: two sampling schemes for the correction of scattered radiation", Med. Phys. Vol 15, p.732-748 (1988) by Wagner, F. C., Macovski, A K and Nishimura D. C. gives an example of an interpolation method which can be used under the present invention.

In an alternate embodiment, this determination can be performed by parametric approximation of scattering, whose parameters will be determined in relation to the regions corresponding to the projection of radio-opaque elements in which only scattering is identified, which then allows determination of X-ray scattering over the entire object O.

Figure 6:
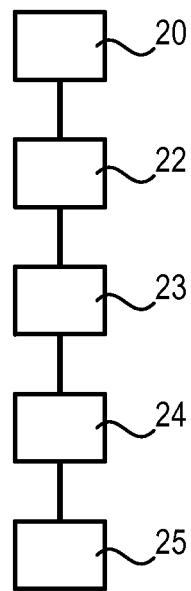

FIG. 6 illustrates an embodiment of a method comprising two additional processing steps.

In this embodiment, the method comprises a pre-processing step 22, prior to extraction step 23, to filter the noise resulting from acquisition step 20 and thereby facilitate the extracting 23 and determining steps 24 of X-ray scattering in the object O.

The method such as illustrated in FIG. 6 further comprises a post-processing step 25 after the determination step 24. Similar to the pre-processing step 22, this post-processing step typically consists of filtering the noise present in the obtained image to achieve a more homogeneous result.

At the pre-processing 22 and post-processing 25 steps, filtering is typically conducted using a low-pass or median filter, or using any other suitable filtering device.

The method such as described therefore allows the determination of X-ray scattering in the object after acquiring a pre-exposure image, and thereby allows precise scatter data to be obtained for a specific object without the need for an additional acquisition. It also avoids deterioration of the final image by not inserting any radio-opaque elements between the object and the source at the time of acquiring the main images used for diagnosis.

Figure 7:
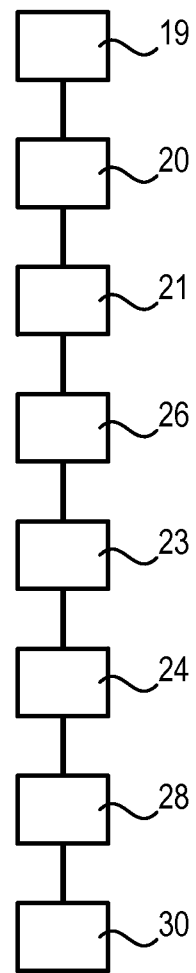
FIG. 7 illustrates an application of an image correction method to a mammography method according to an embodiment of the present invention.

FIG. 7 illustrates a medical imaging method applying the method illustrated in FIG. 5.

The embodiment illustrated in FIG. 7 comprises a positioning step 19 to position the mask 8 between the object O and the X-ray emission source 3, prior to the acquisition 20 of the pre-exposure image.

The method further comprises an acquisition step 20 to acquire the pre-exposure image such as described previously, the pre-exposure image typically being acquired at this step. The method further comprises a removal step 21 to remove the mask so that it no longer lies on the pathway of the X-rays which are to pass through the object O, said removal typically being performed automatically or via an actuator.

The method further comprises a main acquisition step 26 to acquire images resulting from the passing of X-rays through the object using higher doses than the X-ray dose used for acquisition of the pre-exposure image, these doses being determined by means of the data collected at the first acquisition step 20.

The method further comprises an extraction step 23 such as described previously and a determination step 24 such as described previously.

The method further comprises a defining step 28 to define one or more coefficients to scale the contribution of scattered X-ray radiation to the image of the object, these coefficients resulting from the difference between the emitted X-ray dose for acquisition of the pre-exposure image and the X-ray doses emitted for the main acquisition, so as to apply this or these coefficients to X-ray scatter for the X-ray dose emitted when acquiring the pre-exposure image in order to determine scattering in the object O at the doses emitted for the main acquisition; this defining step 28 possibly being carried out before or after the determination step 24. The method further comprises a generating step 30 to generate a final image of the object O, said generation using both the images acquired at the main acquisition step 26 and optionally the first image acquired at the first acquisition step 20. Modelling is typically performed using methods well known to the person skilled in the art not taking X-ray scatter into account; completed by processing to arrive at a final image in which X-ray scatter has been deleted. Processing typically consists of subtracting the previously determined intermediate image and the term of X-ray scatter from the main acquisition image. The final image is thus corrected so as not to show the defects generated by X-ray scatter.

In an alternate embodiment, the medical imaging method may comprise the additional processing steps illustrated in FIG. 6 and already described in the foregoing.

Embodiments of the present invention allow for twofold use of the pre-exposure image.

This pre-exposure image is acquired as is conventional to determine the acquisition conditions for subsequent images used for diagnosis.

However, the invention allows additional use thereof to determine X-ray scatter in the targeted object. The presence of the mask 8 for the acquisition of this pre-exposure image is not penalizing for diagnosis, insofar as this pre-exposure image is not an image used for diagnosis.

Embodiments of the present invention do not therefore require the acquisition of an additional image compared with a conventional mammography method, and allows correction of acquired images by largely enhancing quality.

What is claimed is:

1. A method for correcting at least one image of an object obtained with a mammography system comprising an X-ray emitting source arranged facing a detector, the object being positioned between the source and the detector, the acquisition conditions of the images being determined by using the characteristics of a pre-exposure image of the object, the method comprising:
   acquiring a pre-exposure image of an object to determine the acquisition conditions for main images, the pre-exposure image comprising regions corresponding to the projection of radio-opaque elements, wherein a mask comprising radio-opaque elements is in an acquisition position, the acquisition position being when the mask is in the X-ray pathway leading from the source to the object;
   acquiring the main images resulting from the passing through the object of X-rays at higher doses than the dose used for acquisition of the pre-exposure image, wherein the mask comprising radio-opaque elements is in a retracted position, the retracted position being when the mask is outside of the X-ray pathway leading from the source to the object;
   extracting regions from the pre-exposure image which correspond to the projection of radio-opaque elements; and
   determining the contribution of X-ray scatter at every point of the at least one image of the object, on the basis of the regions extracted from the pre-exposure image.

2. A method for the mammography of an object using a system comprising an X-ray emitting source arranged facing a detector, the object being positioned between the source and the detector, the acquisition conditions of at least one image of the object being determined using the characteristics of a pre-exposure image of the object, the method comprising:
   acquiring a pre-exposure image of the object, the pre-exposure image resulting from the passing through the object of a first dose of emitted X-rays, and comprising regions corresponding to the projection of radio-opaque elements, wherein a mask comprising radio-opaque elements is in an acquisition position, the acquisition position being when the mask is in the X-ray pathway leading from the source to the object;
   acquiring main images resulting from the passing through the object of an at least one dose of emitted X-rays, the at least one dose being greater than the first dose, wherein the mask comprising radio-opaque elements is in a retracted position, the retracted position being when the mask is outside of the X-ray pathway leading from the source to the object;
   extracting regions from the pre-exposure image which correspond to the projection of radio-opaque elements;
   determining X-ray scatter in the object from the regions extracted from the pre-exposure image;
   defining coefficient(s) resulting from the difference in dose between the first dose of emitted X-rays and the at least one dose of emitted X-rays that are great than the first dose;
   using the coefficient(s) to scale the contribution of X-ray scatter to the image of the object; and
   subtracting the term of scattered X-ray radiation from the main images to obtain a final scatter-free image.

3. A system for the mammography of an object using X-rays, the system comprising:
   an X-ray emission source;
   a detector arranged facing the source, wherein the object is positioned between the source and the detector;
   a mask comprising radio-opaque elements that is formed in a flexible material, and is wound around a rotating drum whose rotation causes movement of the mask; and
   a processing unit comprising a computer configured to extract regions from a pre-exposure image of the object which correspond to the projection of radio-opaque elements and to determine the contribution of X-ray scatter at every point of at least one image of the object on the basis of the regions extracted from the pre-exposure image,
   wherein the pre-exposure image of the object is acquired when the mask comprising radio-opaque elements is in an acquisition position, the acquisition position being when the mask is in the X-ray pathway leading from the source to the object, and
   wherein main images resulting from the passing through the object of X-rays at higher doses than the dose used for acquisition of the pre-exposure image are acquired when the mask comprising radio-opaque elements is in a retracted position, the retracted position being when the mask is outside of the X-ray pathway leading from the source to the object.

4. The system according to claim 3, further comprising a mechanical actuator, wherein the mechanical actuator moves the mask comprising radio-opaque elements between the acquisition position and the retracted position.

5. The system according to claim 4, wherein the mask further comprises at least one radio-opaque element arranged substantially radially relative to the object so as to at least partially cover the object.

6. The system according to claim 4, wherein the mask further comprises at least one radio-opaque element arranged substantially aligned on a border of the at least one image so as to at least partially cover the organ.

7. The system according to claim 1, wherein the mask comprising radio-opaque elements is formed in a flexible material, and is wound around a rotating drum whose rotation causes movement of the mask.

8. The system according to claim 4, wherein the radio-opaque elements of the mask cover no more than 10% of the projection surface of the X-rays emitted by the source.

9. The method of claim 1, comprising:
defining coefficient(s) resulting from a difference in dose between the dose used for acquisition of the pre-exposure image and the higher dose used to acquire the main images;
using the coefficient(s) to scale the contribution of X-ray scatter to the image of the object; and
subtracting the term of scattered X-ray radiation from the main images to obtain a final scatter-free image.

* * * * *

UNITED STATES PATENT AND TRADEMARK OFFICE
CERTIFICATE OF CORRECTION

PATENT NO. : 8,867,700 B2  
APPLICATION NO. : 13/281828  
DATED : October 21, 2014  
INVENTOR(S) : Carton et al.

Page 1 of 1

It is certified that error appears in the above-identified patent and that said Letters Patent is hereby corrected as shown below:

In The Specification

In Column 3, Line 27, delete "invention," and insert -- invention. --, therefor.

In Column 4, Line 63, delete "object O The" and insert -- object O. The --, therefor.

In Column 4, Line 67, delete "elements elements 10," and insert -- elements 10, --, therefor.

In Column 5, Line 32, delete "via," and insert -- via --, therefor.

In Column 6, Line 1, delete "Nishimura D.C." and insert -- Nishimura D.G. --, therefor.

Signed and Sealed this  
Fifth Day of May, 2015

Michelle K. Lee  
*Director of the United States Patent and Trademark Office*